(12) United States Patent
Rhodes et al.

(10) Patent No.: US 11,474,078 B2
(45) Date of Patent: Oct. 18, 2022

(54) FINGERPRINTING AND ANALYZING GEMSTONES

(71) Applicant: Gemological Institute of America, Inc., Carlsbad, CA (US)

(72) Inventors: George Wyatt Rhodes, Corrales, NM (US); Sally Catherine Magana, Laguna Hills, CA (US)

(73) Assignee: Gemological Institute of America, Inc. (GIA), Carlsbad, CA (US)

( * ) Notice: Subject to any disclaimer, the term of this patent is extended or adjusted under 35 U.S.C. 154(b) by 260 days.

(21) Appl. No.: 16/489,339

(22) PCT Filed: Feb. 27, 2018

(86) PCT No.: PCT/US2018/019956
§ 371 (c)(1),
(2) Date: Aug. 27, 2019

(87) PCT Pub. No.: WO2018/160563
PCT Pub. Date: Sep. 7, 2018

(65) Prior Publication Data
US 2020/0011837 A1 Jan. 9, 2020

Related U.S. Application Data

(63) Continuation of application No. 15/444,736, filed on Feb. 28, 2017, now Pat. No. 10,386,337.

(51) Int. Cl.
*G01N 29/12* (2006.01)
*G01N 29/24* (2006.01)
(Continued)

(52) U.S. Cl.
CPC ......... *G01N 29/12* (2013.01); *G01N 29/2437* (2013.01); *G01N 29/4454* (2013.01);
(Continued)

(58) Field of Classification Search
CPC ............... G01N 29/12; G01N 29/2437; G01N 29/4454; G01N 29/46; G01N 2291/0232; G01N 2291/102
See application file for complete search history.

(56) References Cited

U.S. PATENT DOCUMENTS

| | | |
|---|---|---|
| 5,062,296 A | 11/1991 | Migliori |
| 5,495,763 A | 3/1996 | Rhodes et al. |

(Continued)

FOREIGN PATENT DOCUMENTS

| | | |
|---|---|---|
| CN | 104599392 | 5/2015 |
| CN | 104599392 A | 5/2015 |

(Continued)

OTHER PUBLICATIONS

International Search Report and Written Opinion received for PCT Patent Appln No. PCT/US2018/019956 dated May 14, 2018, 12 pages.

(Continued)

*Primary Examiner* — Tarun Sinha
(74) *Attorney, Agent, or Firm* — DLA Piper LLP (US)

(57) ABSTRACT

The embodiments disclosed herein relate to the examination of gemstones including diamonds, both cut/polished and rough, using the technology of Resonant Ultrasound Spectroscopy. The resonant frequencies are obtained by mechanically causing the stone to vibrate using a swept sine oscillator, sensing the resonance vibrations, and displaying the spectrum to yield a pattern describing the stone. The resonance fingerprints can be used to both track an individual stone to verify its integrity or to grade a rough stone to establish potential value.

20 Claims, 11 Drawing Sheets

(51) Int. Cl.
*G01N 29/46* (2006.01)
*G01N 29/44* (2006.01)

(52) U.S. Cl.
CPC ..... *G01N 29/46* (2013.01); *G01N 2291/0232* (2013.01); *G01N 2291/102* (2013.01)

(56) References Cited

U.S. PATENT DOCUMENTS

| | | | |
|---|---|---|---|
| 5,922,956 A * | 7/1999 | Rhodes | G01N 29/42 |
| | | | 73/579 |
| 8,903,675 B2 | 12/2014 | Jauriqui et al. | |
| 9,304,112 B2 | 4/2016 | Rhodes et al. | |
| 10,386,337 B2 | 8/2019 | Rhodes | |
| 10,788,460 B2 | 9/2020 | Rhodes | |
| 2005/0117145 A1 * | 6/2005 | Altman | G01N 21/87 |
| | | | 356/30 |
| 2007/0005269 A1 | 1/2007 | Mitchell | |
| 2008/0231833 A1 | 9/2008 | Shlezinger et al. | |
| 2010/0207602 A1 | 8/2010 | Loverich | |
| 2013/0096881 A1 | 4/2013 | Jauriqui et al. | |
| 2013/0262894 A1 * | 10/2013 | Lee | G06F 1/3296 |
| | | | 713/322 |
| 2014/0002203 A1 | 1/2014 | Liu | |
| 2014/0298611 A1 | 10/2014 | Conrad | |
| 2014/0298911 A1 | 10/2014 | Rhodes et al. | |
| 2015/0300993 A1 | 10/2015 | Prest | |

FOREIGN PATENT DOCUMENTS

| | | |
|---|---|---|
| JP | H04204250 A | 7/1992 |
| JP | H05504840 A | 7/1993 |
| JP | 5984127 B2 | 9/2016 |
| JP | 2017022310 A | 1/2017 |
| WO | 2012/058842 A1 | 5/2012 |
| WO | WO-2012058842 | 5/2012 |

OTHER PUBLICATIONS

International Search Report and Written Opinion received for PCT Patent Application No. PCT/US2018/019956, dated May 14, 2018, 12 pages.

* cited by examiner

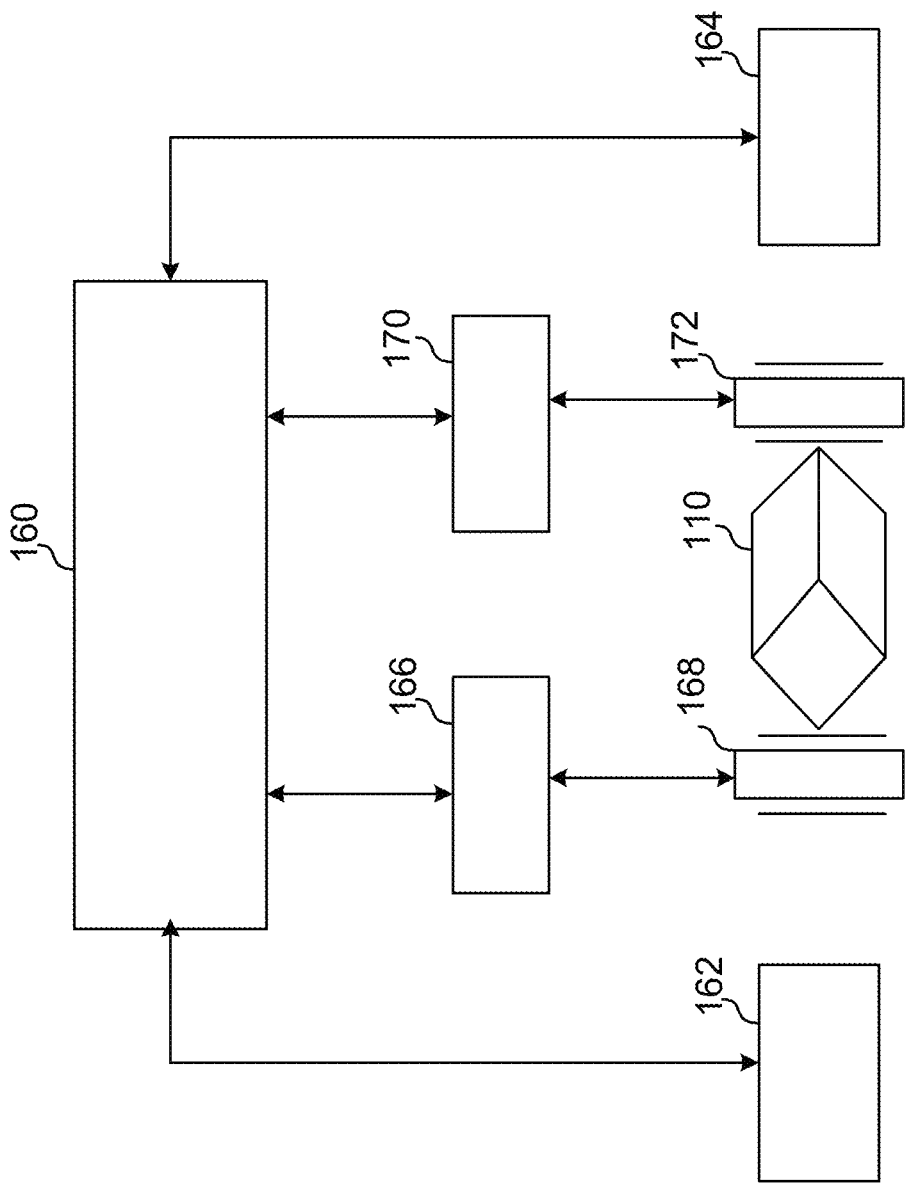

FINGERPRINTING AND ANALYZING GEMSTONES

CROSS REFERENCE

This application claims priority of International application no. PCT US18/19956 filed on Feb. 27, 2018, which in turn claims priority to U.S. utility patent application Ser. No. 15/444,736 filed Feb. 28, 2017, both of which are incorporated herein by reference in their entireties.

FIELD

This application relates to the field of nondestructive testing of gemstones, for example diamonds in any condition including but not limited to cut, polished, and/or rough stones to create a digital identification for a stone. Some embodiments include analysis of gemstones to identify physical characteristics which may be used to sort stones for potential value.

BACKGROUND

Diamonds are mined as rough stones from which they undergo examination to determine their value as a gem or for industrial use. Fewer than 25% of mined diamonds are worthy of cutting and polishing to yield gems for jewelry. About 40% of the remaining population still have value as industrial diamonds for machine tools, and the rest is ground into dust to provide coatings for grinding applications. Thus, making these determinations efficiently and accurately is useful.

Rough stones generally exist in two conditions: coated and uncoated. Coated stones have a layer of polycrystalline diamond, different from the predominant crystal structure, rendering them opaque. This may interfere with optical inspection, as any cracks, or inclusions cannot be seen or are harder to see with human inspection. A reliable sorting system would be of great use.

Additionally or alternatively, as high value items, gemstones may be stolen. There is a need to identify these stones, at their origin, for later use in identity confirmation. Additionally, or alternatively, as high value items, gemstones often change custody over time. Once a stone is cut and polished, there is a desire to identify the object to ensure its integrity and identity. The systems and methods here fulfill these needs and others. While many examples herein are directed to analysis and identification of diamonds, it should be expressly understood that the invention is not so limited and is applicable to a wide variety of other gemstones including, without limitation, corundum, tourmaline, beryl, and tanzanite.

SUMMARY

System and methods here may include mounting a stone to be tested on a test stand, contacting the stone by at least two piezoelectric transducers, vibrating at least one of the piezoelectric transducers through a predetermined range of interest to produce resonances in the stone, sensing the resultant resonances at least one of the piezoelectric transducers, amplifying bot of the transducer signals to meet signal-to-noise requirements, by controlling the resonant ultrasound spectrometer containing a processor and memory, with algorithms, the in-phase and quadrature components of the resonance signal to generate a resonance data, thus causing display of the resonance data in a user interface on the controlling computer.

In one example, systems, methods, and non-transitory computer readable media here include using a chip, with a processor and memory, as a signal generator and a signal processor for sending an input signal to a first input transducer, where in use, the first input transducer is contacting a stone under evaluation, then receiving a resonance signal from a second receiver transducer, where in use, the second receiver transducer is contacting the stone under evaluation, then stepping the input signal through a range of input frequencies, then receiving a range of received signals. In some example embodiments, the chip is then used for processing, with algorithms, the range of received signals and sending the processed range of received signals for the stone under evaluation to a computer for display.

Another example system and method here may include mounting a stone to be tested on a test stand, contacting the stone by at least two piezoelectric transducers, vibrating one piezoelectric transducer through a predetermined range of interest to produce resonances in the stone, simultaneously sensing the resultant resonances another identical piezoelectric transducer, amplifying both transducer signals to meet signal-to-noise requirements, by controlling the resonant ultrasound spectrometer containing a processor and memory, with algorithms, the in-phase and quadrature components of the resonance signal to generate a resonance data, thus causing display of the resonance data in a user interface on the controlling computer.

Systems and methods here include a computer with a processor and a memory, in communication with a first input transducer and a second receiver transducer, through the resonant ultrasound spectrometer, for sending an input signal to the first input transducer. In some example embodiments, the first input transducer is contacting a stone under evaluation. In some example embodiments, the computer may be used as a graphical interface for observing a resonance signal from the second receiver transducer. Additionally or alternatively, in some example embodiments, the resonant ultrasound spectrometer may be used for amplifying both the excitation and received signals, and processing, with algorithms the received signal. And additionally or alternatively, in some example embodiments, the computer may be used for observing the resonance data for the stone under evaluation based on the processed signals.

BRIEF DESCRIPTION OF THE DRAWINGS

In order to understand the invention and to see how it may be carried out in practice, embodiments will now be described, by way of non-limiting example only, with reference to the accompanying drawings, in which:

FIGS. 1A, 1B, and 1C are example hardware system diagrams of hardware which may be used to implement the methods described herein.

DETAILED DESCRIPTION

Figure 1A:
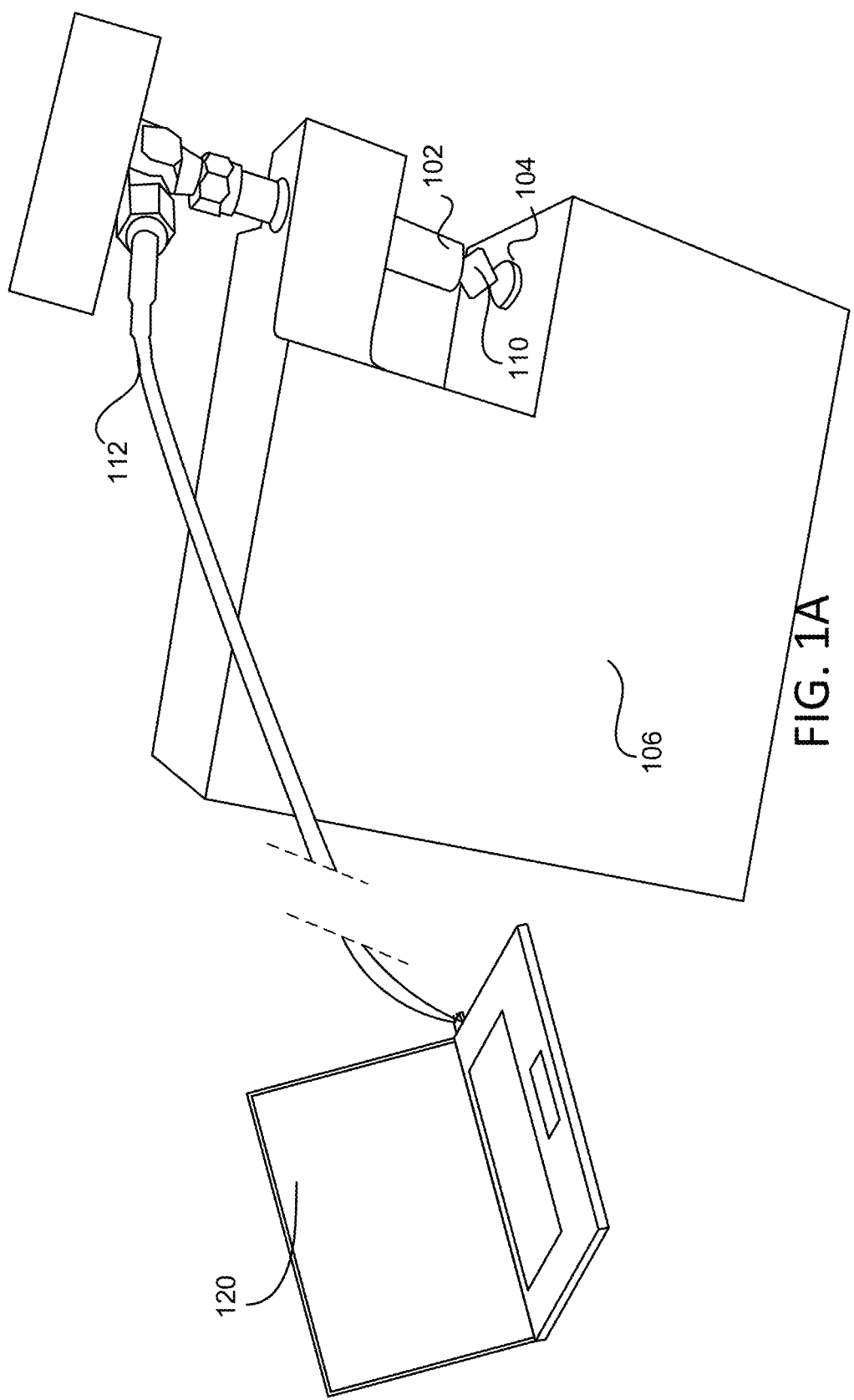

Reference will now be made in detail to embodiments, examples of which are illustrated in the accompanying drawings. In the following detailed description, numerous specific details are set forth in order to provide a sufficient understanding of the subject matter presented herein. But it will be apparent to one of ordinary skill in the art that the subject matter may be practiced without these specific details. Moreover, the particular embodiments described herein are provided by way of example and should not be used to limit the scope of the invention to these particular embodiments. In other instances, well-known data structures, timing protocols, software operations, procedures, and components have not been described in detail so as not to unnecessarily obscure aspects of the embodiments of the invention.

Overview

Diamonds are mined as rough stones from which they undergo examination to determine their value as being gem quality, or of two different industrial qualities. But due to the technical hurdles of analyzing stones close to the mine source, many times, stones are transacted multiple times before being properly analyzed and categorized for processing and cutting. Further, identification of such stones may be useful. Gemstones are often cut and polished to very similar measurements that can make it difficult to distinguish among diamonds that are similar weight, cut to similar proportions. Gems such as diamonds with very high clarity have very few internal features that can assist in distinguishing similar diamonds and often the presence or absence of internal features cannot be well represented quantitatively. Stones can get mis-identified and confused with one another.

Systems and methods such as those described herein allow for reliable analysis for both cut and/or polished stones as well as some rough diamonds. Additionally, or alternatively, systems and methods here may be used to create a digital identifier of individual stones which may be used to later identity an individual stone and/or verify such stones upon later recovery and/or tracking.

Such analysis and identification of stones may be accomplished by applying the systems and methods here, which invoke the use of Resonant Ultrasound Spectroscopy (RUS). RUS may refer to the application of energy such as mechanical vibration to a stone using an exciter at a specific mechanical force and frequency input and then receiving energy including any resonances produced by the stone. In some examples, a range of input frequencies may be imparted, in order to receive a range of output responses which may be graphed and otherwise analyzed. In other examples, a resonance frequency or multiple resonance frequencies are detected within the range of received signals. These resonances are vibrations much higher than the noise floor demonstrated at other frequencies and may be used as described herein to identify or otherwise analyze a stone.

These received RUS signal examples may reflect the physical shape, density, structural abnormalities, and/or elastic properties of the individual stone, and thereby help identify these characteristics in the stone. And in some examples, where the density is nearly identical, for example, as is the case with all or most diamonds whether cut and polished or rough, the particular resonances may then be the result of the geometry and even elastic properties of the stone. Thus, even similarly composed stones may be differentiated by other properties.

The received signal graphs for each analyzed stone may be stored and catalogued so that it may be used to compare to a later graph for identification of that stone or even portions of a stone. In some example embodiments, such a unique signal which may be used for identification may be considered or referred to as an identifier or "fingerprint" of the stone.

It should be noted here that the term "fingerprint" is not intended to be limiting. The term fingerprint, or fingerprinting may be used to refer to a unique identifier which may be stored and used to later identify the same object, and/or determine certain characteristics of the stone. In some examples, the fingerprint is a graph or chart of the received resonant energy from an individual stone, used to analyze and/or identify that stone. Much like each person having a different fingerprint, based on the ridges on the skin of the human finger, unique physical properties of other objects may be obtained, analyzed, and used to later identify a stone. In the examples here, such fingerprints, or unique identifiers, may be found using resonance techniques as described.

While many examples herein are directed to analysis and identification of diamonds, it should be expressly understood that the invention is not so limited and is applicable to a wide variety of other gemstones including, without limitation, corundum, tourmaline, beryl, and tanzanite.

System Examples

Additionally, or alternatively, in some example embodiments, the system(s) which may be used to perform the methods described here, may include certain hardware and computer resources, working together. FIG. 1A show example arrangements of hardware which may be used in the example embodiments herein to apply energy to a stone, and thereby receive the response return including any resonance energies. These responses may be processed and subsequently displayed in a user interface and/or otherwise analyzed.

In FIG. 1A, at least two transducers 102, 104 are shown in a system 106 coupled to or otherwise contacting a stone under examination 110. The transducers 102, 104 may be connected to or otherwise in communication with a computer 120 by a wired 112 or wireless (not pictured) connection. This computer 120 may send commands and/or signals for the input transducer 102 to impart energy on the stone 110. The computer 120 may also receive data from the receiving transducer 104 in order to analyze the resonance patterns from the stone 110 as discussed herein.

The transducers 102, 104 may include piezoelectric components that may either impart energy and/or receive energy. In some examples, the imparted or applied energy may be in the form of mechanical vibrations imparted by a first piezoelectric transducer 102 to a stone 110. In some example embodiments, the input energy may include a specific set or range of ultrasonic frequencies as described herein.

In preferred embodiments, a second transducer 104 may be used to sense, receive, or otherwise detect the mechanical responses of the stone 110 including any resonant responses. The signals from these receiving transducers 104 may be sent to any of various computer 120 hardware for amplification, processing, charting and/or otherwise analyzing. In some examples, the computer 120 may serve as a connected dynamic signal analyzer which receives the input and determines the relevant resonances that adequately describe the conforming spectrum. In some examples, the signal generator, amplifiers, and spectrometers are separate component parts as described herein.

By knowing the input frequency range, and by receiving a specific range of signal responses for each individual stone, a repeatable method may be utilized to analyze and/or identify a stone using the systems and methods described herein. In some example embodiments, the resultant signal may be graphically displayed on a user interface as shown for example in FIG. 2. In some example embodiments, the resultant signal may be graphed, digitally mapped, or otherwise sampled and stored for later comparison to other signals. In some example embodiments, this resultant signal may be referred to as the resonance fingerprint of the stone.

In the example of FIG. 1A, an integrated RUS system is contained within the computer 120 including but not limited to a signal generator, amplifiers, and spectrometer. In some example embodiments, a separate RUS system is located between and in communication with the transducers 102, 104 and the computer 120. In such example embodiments, the RUS system (not pictured in FIG. 1A) would send commands and/or generate signals for the input transducer 102 including amplification of the signal as well as receive a signal from the receiving transducer 104 and amplify and process that received signal for a spectrometer to process. The computer 120 in such examples may only be used to display the resultant graphs of the processed signals and/or store data. Any combination or permutation of hardware components in various housings and peripheral connections may be utilized as described herein.

It should be noted that in some examples, the orientation of the stone under examination 110 between the transducers 102, 104, may affect the output of an RUS analysis. Example orientations include, table-to-culet or girdle-to-girdle orientations of the stone 110. Each orientation may provide advantages and disadvantages in terms of reproducibility in peak detection on subsequent scans of the same diamond and distinguishing between diamonds with nominally similar characteristics. Thus, orientation of each stone 110 for a particular RUS analysis may need to be annotated or otherwise included in any graph or report.

Figure 1B:
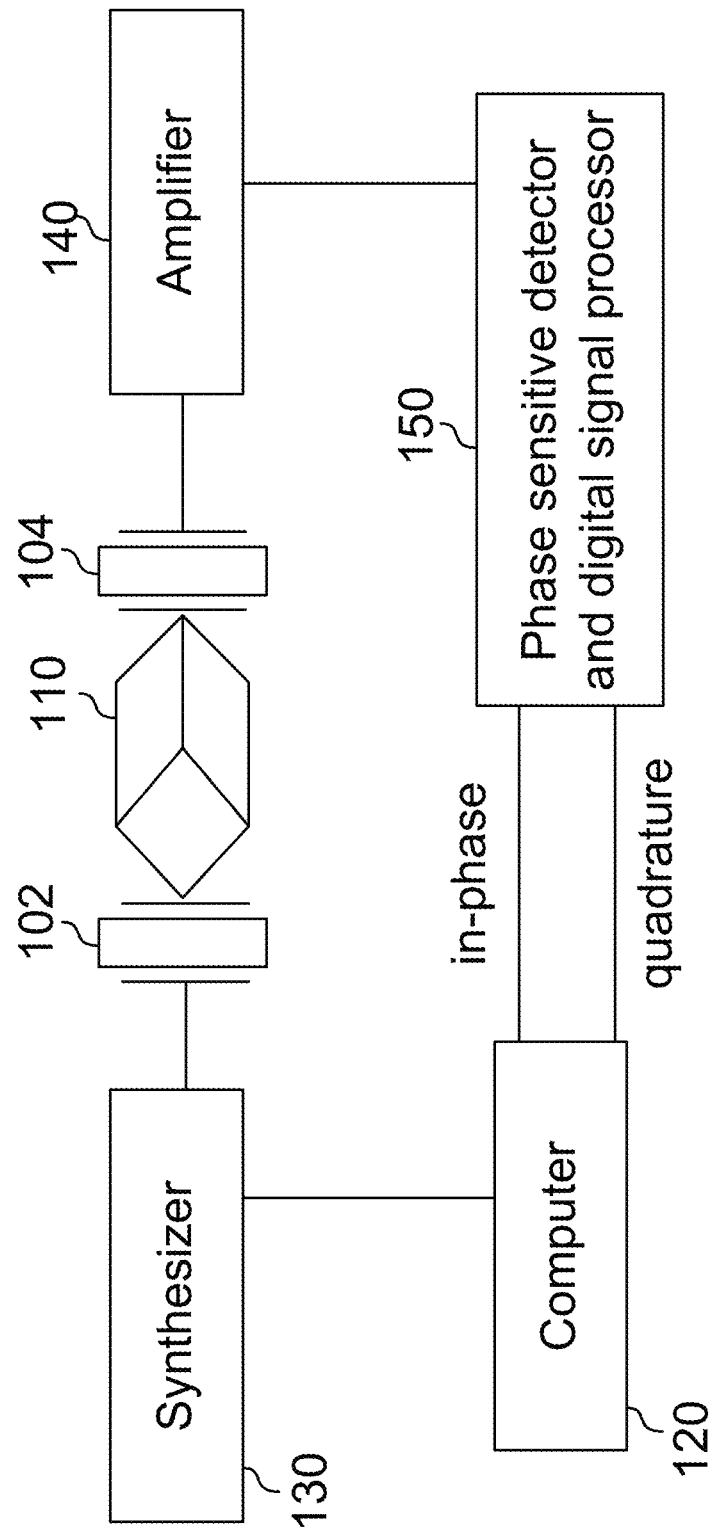

FIG. 1B shows an example schematic diagram embodiment, alternatively or in addition to the computer arrangement of FIG. 1A. In FIG. 1B, the computer 120 may include a display, data storage, and/or command sender arrangement to the rest of the system. In some examples as shown in FIG. 1B, the system may include a frequency synthesizer 130 in communication with the computer 120 where the synthesizer 130 is configured to produce an electrical signal and/or range of signals when given a command by the computer 120. The synthesizer 130 may be connected to a piezoelectric crystal 102, which converts the received electrical signal from the synthesizer 130 into a mechanical vibration. Such an example mechanical input transducer 102 may be contacted to a stone 110 to cause it to vibrate. As described below, a range of frequencies may be imparted on the stone 110 by the input transducer 102.

In response to the imparted frequencies, the stone 110 will vibrate and an additional receiving transducer 104 in contact with the stone 110 may be configured to sense the resulting vibrations and send an electric signal to an amplifier 140 for processing. In some examples, such resulting vibrations may result in a range of responses including specific resonant peaks, which may be sensed and graphed or sampled as described herein.

In some examples, the amplified signal is then processed by a phase sensitive detector and digital signal processor 150 and both the in-phase and out-of-phase or quadrature signals may be sent to the computer 120 for processing and analysis. In some example embodiments, a process is used to add the signals. In some examples, the square root of the sum of squares is used to process the signals. For example:

$$Sum = \sqrt{(1\ signal^2) + (2\ signal^2)}$$

Figure 2:
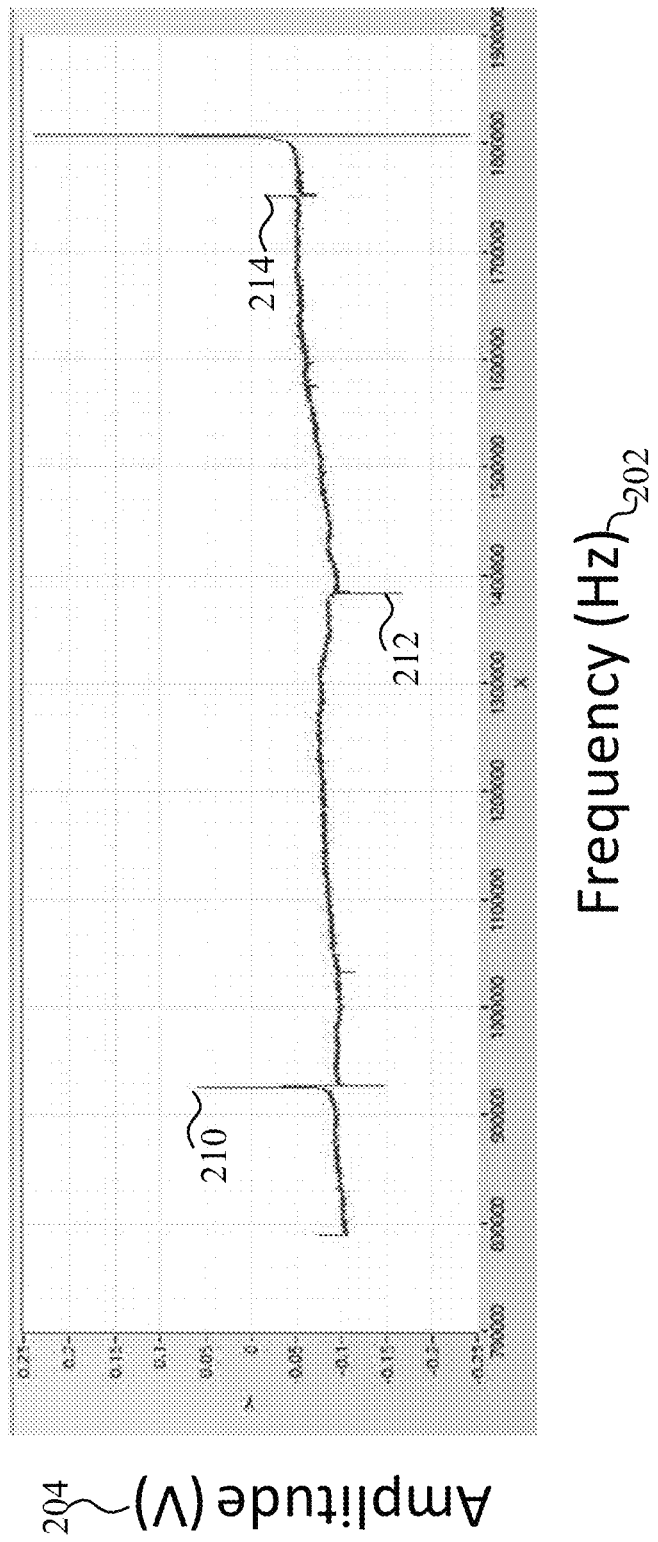
FIG. 2 is an example charts which may be ascertained using the systems and methods described herein.

The resultant energy graph may then be displayed on a user interface computer 120 as a chart of an all positive set of peaks instead of analyzing both negative and positive resonance peaks as shown, for example, in FIG. 2.

It should be noted that the components in FIG. 1B such as the synthesizer 130, amplifier 140, phase sensitive detector and digital signal processor 150 may also be part of or work in the computer 120 itself. In other words, these component parts in FIG. 1B may be included in the computer 120 in some embodiments.

FIG. 1C is another hardware configuration example, in addition to, or in the alternative to FIG. 1A and FIG. 1B. The example of FIG. 1C includes an application specific integrated circuit 160 (ASIC) and/or system on chip with integrated memory such as but not limited to ROM, RAM, EEPROM, flash memory, and processors including microprocessors. Some examples may include arrangements such as those in the Red Pitaya system, but other arrangements and hardware may be used in addition to or in place of such a system on chip. Such a system on chip 160 may receive power such as but not limited to a 5 volt power source 162. The chip 160 in some example embodiments may also be coupled to and/or in communication with a computer 164 by way of an Ethernet, other wired, or even wireless communication arrangement. In these example embodiments, the system on chip 160 may serve as the signal generator and signal processor for the RUS system.

In such example arrangements as shown in FIG. 1C, the system on chip 160 may also be in communication with and/or coupled to a charge amplifier 166. Such a charge amplifier 166 may serve as an amplifier for the input signal to the stone under evaluation 110. Such a charge amplifier 166 may be coupled to and/or in communication with the first transducer 168 which may vibrate when it receives an input signal from the charge amplifier 168 to deliver the input frequency to the stone under evaluation 110 as described herein. The system on chip 160 may also be coupled to and/or in communication with another amplifier, the RUS amplifier 170 which may serve as the amplifier for the received frequencies from the second transducer 172. When in use, this second transducer, or receive transducer 172 may be in communication with and/or touching the stone under evaluation 110 and receive through its piezoelectric arrangement, the frequencies of the stone under evaluation 110 including any resonant frequencies. This received signal may then be amplified by the RUS amplifier 170 and send to the chip 160 for processing. In the example of FIG. 1C, the system on chip 160 serves as the signal generator and the signal processor, it then sends the computer 164 the received and processed data from the stone under evaluation 110 to analyze, graph, and display.

In some example embodiments, the chip 160 and/or the computer 164 may be in communication with a network such as the Internet. Through such a connection, the chip 160 and/or the computer 164 may interact with software hosted on a network server. In some example embodiments, the software used for the RUS system is stored on the local computer 164 and/or chip 160. In some example embodiments, the software is stored on both the local computer 164 and/or chip 160 as well as accessible over the network.

It should be noted that the embodiments of FIGS. 1A, 1B and 1C may be combined and utilized in various combinations. The embodiments are not necessarily exclusive of one another, and are not intended to be limiting. The hardware disclosed herein may be assembled in various forms and combinations, alternatively or additionally, in order to carry out the methods disclosed herein.

More details on the signal analysis and generation are described below. Further discussion of the computer is found in FIG. 7.

Received Resonant Energy Overview

Gemstones such as diamonds are solid objects. A solid object may be excited by an exciting mechanical input (transducer) at any number of frequencies, such as but not limited to ultrasonic frequencies as described herein. In some examples, such a range of ultrasonic frequencies may be used to excite a gemstone. The response to the applied exciting energy may be a resonance of the object at certain frequencies. Resonance is the tendency of an object to oscillate at a greater amplitude at some frequencies more than at others. These are known as the object's resonant frequencies (or resonance frequencies) and may be functions of the square root of the stiffness over the mass, the density of the material and the shape, including all dimensions.

$$Frequency = \sqrt{stiffness/mass}$$

Applying a spectrum or range of exciting input energy to a solid object may allow for these resonance frequencies to be identified for an individual object, such as a gemstone. In some examples, the range may be a swept sine method, whereby sinusoidal frequencies are swept or stepped through. Such a range of applied frequencies may result in a received spectrum including any identifiable resonance which are inherent in the solid object that show up as amplitude spikes, as well as where there is no amplitude, indicating that the stone has no resonance at that frequency.

As discussed, solid object resonances may be affected by, or the result of, the object's geometry, including shape, and/or the elastic properties of the solid object. In some examples, the shape and dimensions of the stone's cut produce the specific resulting response and therefore its resonance peaks which may be charted. This is especially the case for diamonds that consist of just one single crystal. In such examples, the density and elastic properties may be known values, and therefore the resonances may be governed by the absolute geometry along with subtle contributions of the aforementioned inclusions and inhomogeneities.

This allows the application of RUS to produce a fingerprint unique to the cut/polished sample solely due to the physical shape including such as its faceting dimensions or impacted by internal inclusions such as crystals, "feathers," or other physical aspects that can impact the resonances. With rough gemstones, cracks and other inclusions are often present which impact the structural rigidity and easily observable with RUS both through the quantity of detected resonances and the Q values (peak widths discussed below) of the detected resonance. This characterization aids in sorting rough diamonds due to the structural properties, while also providing a fingerprint identifier for those with rigid structures. Thus, in some examples, even the elastic properties of the stone may be measured in the same way, for stones with many inclusions and defects. In such examples, stones containing many inclusions or flaws may be identified as well.

An example of a resonance graph of a cut, polished diamond of a single crystal is shown in FIG. 2. This chart includes applied exciting frequencies from 0.8 MHz to 1.8 MHz shown along the X axis 202. The resultant resonance peaks in the example are shown on a Y axis of amplitude 204. In the example, peaks are observed at approximately 0.93 MHz 210, 1.38 MHz 212, and 1.75 MHz 214. This signature or pattern may be used as described here, for this individual stone.

Because diamonds have essentially similar densities, approximately 3.5 g/cm3, and single crystals have the same elastic constants, except when cracks are present, the shapes of the crystals may differ and provide different resonant fingerprints. Independent of how a resonance spectrum is created, it can be measured and compared with the archived fingerprint to observe whether or not it has been altered.

In some examples, multiple crystals can exist in a single stone. The systems and methods described here may be used to ascertain how many crystals appear in a single stone for identification purposes. As discussed above, approximately ten resonances may be observable in a specified frequency range for a single crystal. When twice, or three times that number is observed as shown in the example fingerprints in FIG. 3, two or more crystals may be within that single stone, in some examples. Such analysis may assist an examiner to value the diamond and/or identify it.

In some examples, the weight of the stone may even be approximated from such methods using the square root of the mass over two for the lowest resonance frequency.

Absolute Frequency Resonance Examples

Using the methods described herein, a plot of the resultant, received vibrations from the stone, as absolute frequency versus relative amplitude may be made, as a range or spectrum of frequencies are imparted on a sample stone. Instead of imparting just one impact frequency onto a stone, which would result in a poor signal to noise ratio and all resonances at once, a step through of a range of specific frequencies may be received and plotted. This range of frequencies imparted on a stone, in order to find the resultant resonance peaks may be graphed on the X axis 302 and resultant resonance may be graphed on the Y axis 304, as shown in FIG. 3. By repeating the same range of frequencies on different stones, an identifiable graph (including a table of frequencies), or "fingerprint" may be generated for each, with the resonant peaks charted for analysis and comparison.

FIG. 3 shows an example graph of resultant frequencies for a 0.50 carat diamond given a flawless grade. The graph shows that there are 10 peak resonances for this particular stone's response to imparted energy as it moves from 1.0 MHz through to 3.0 MHz. Such a resultant graph, and specifically the parameters for the peak resonances, may serve as a fingerprint for this diamond, as described herein.

In some examples, the range of the frequencies to be imparted on a stone may be determined based on the shape and/or size of the stone. For example, for larger stones (e.g. >1 carat) a lower frequency may be used as the input frequency than for smaller stones (e.g. 1 carat or less) which may result in a resultant spectrum with enough peak resonances to properly identify a stone. For example, for a 5 carat or 10 carat stone, a 0.5 MHz frequency sweep may be useful, whereas for a 1 carat stone, a range of 1-4 MHz may be preferred. And because larger stones (>1 carat) may produce many more resonance peaks using the systems and methods here, it may be possible, but not necessary to begin a sweep at lower frequencies such as 0.2-0.3 MHz.

In some examples this range of frequencies that are imparted by the transducer to fingerprint a stone may vary depending on the size and/or dimensions of the stone. In some examples, the range of imparted frequencies may be between 1 MHz and 5 MHz. In some examples, between 0.8 MHz and 1.8 MHz. In some examples, the range is between 1 MHz and 4 MHz. Larger stones may require lower frequencies than smaller stones to achieve a quantity of peaks necessary for comparison.

The range of examination between 0.8 MHz and 4 MHz may be appropriate for diamonds between 5 to 0.5 carat (a larger stone has the lowest lying resonance at a lower value than a smaller one). For much larger stones the range of examination may change to a lower frequency.

In some examples, the imparted frequencies are stepped through the range as described above, in order to achieve the range of resultant resonant peaks for graphing. In such examples, the step of frequencies that are imparted by the transducer on a stone may be set such that a maximum number of resonant peaks may be charted, while an efficient use of time and resources is utilized for real world testing conditions. For example, a step that is too large may skip over resonance frequency peaks of a stone and those peaks may be missing in the fingerprint. But a step that is too small may take too long to graph. Thus, various examples here have been shown to be a good balance of accuracy in finding many peak resonances and efficiency in not taking too much time or resources. In some examples, the step may be 100 Hz. In some examples, the step may be 200 Hz. In some examples, steps of 20 Hz may be used. In some examples, a step between 15 and 25 Hz may be used. In some examples, steps of 2 Hz may be used. However, it should be noted that any range of steps may be used to traverse the spectrum of frequencies and thereby achieve a graph of resonance peaks.

Example Resonance Graphs

Various figures here show example fingerprints received and processed using the systems and methods described here. The examples are not intended to be limiting by examples of various fingerprints that may be ascertained.

Figure 3A:
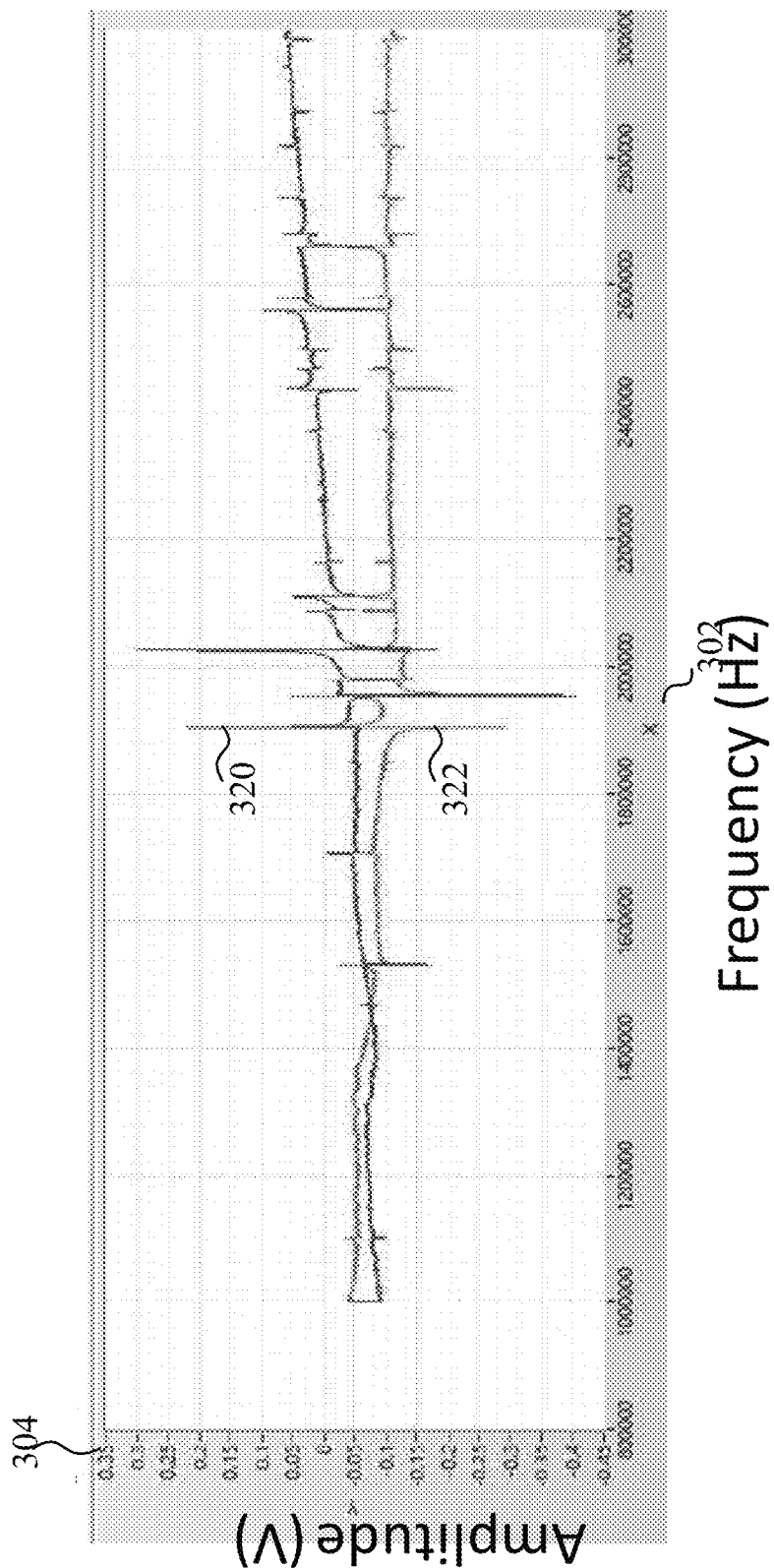
FIGS. 3A and 3B are example charts of various subjects which may be ascertained using the systems and methods described herein.

FIG. 3A shows an example fingerprint of a rough uncoated diamond, simple line shapes, high Q's are evident (as described herein). The graph is representative of gem quality with perhaps more than 1 crystal in the stone. Further examination may be necessary. Two traces are shown here corresponding to both the in-phase 320 and quadrature 322 components of the resonances.

Figure 3B:
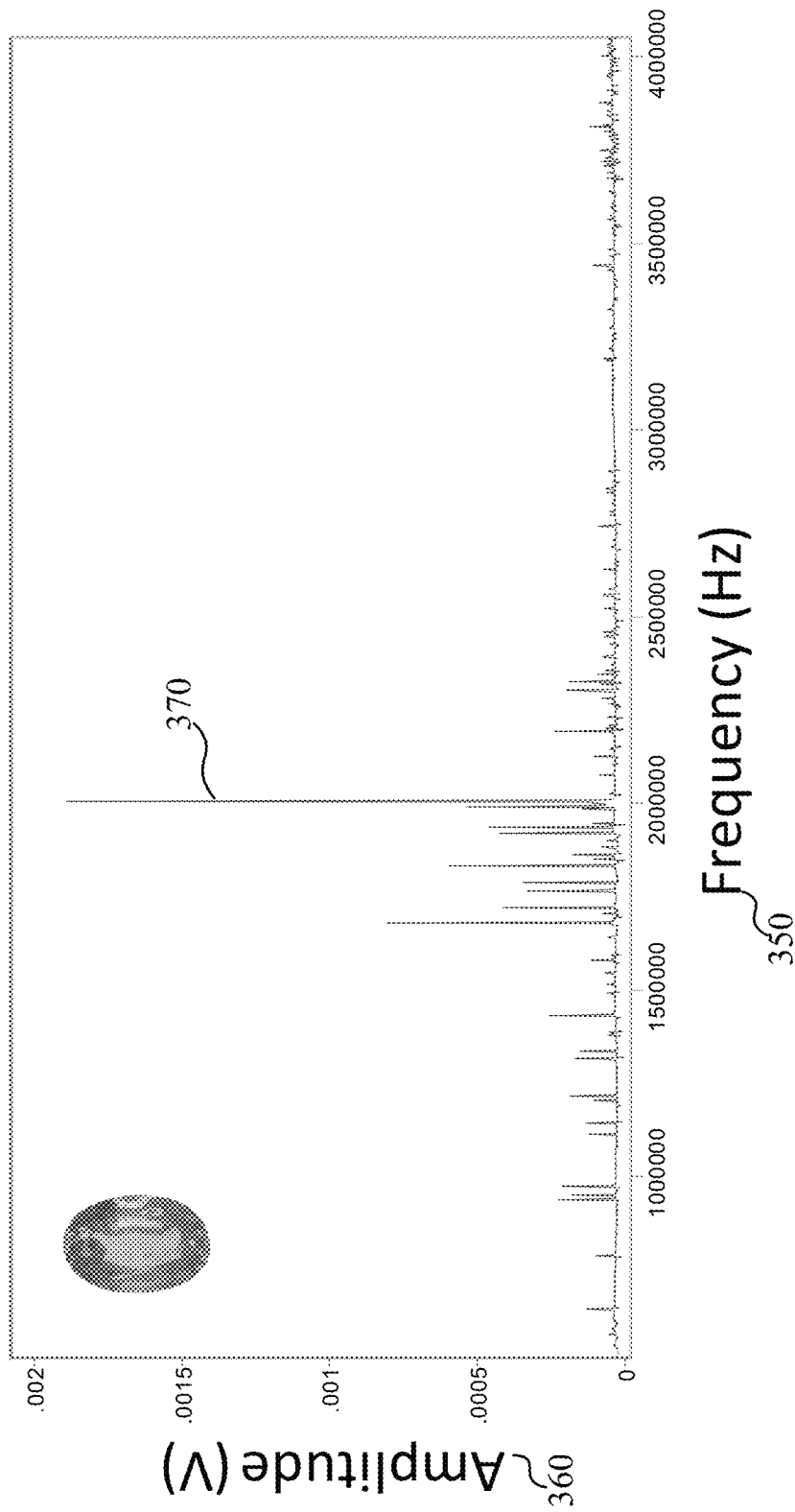

FIG. 3B shows an example RUS fingerprint of a gemstone other than for a diamond. Using the systems and methods here, discernable fingerprints may be ascertained from any various non-diamond stones similarly to how they are ascertained for diamonds as described herein. The examples of diamond and sapphire are not intended to be limiting, and any gemstone may be similarly fingerprinted.

It should be noted that the elastic constants for diamond represent the hardest material known. All other stones are softer, thus the resonant frequencies of the same size stone, will have much lower frequencies than diamond. Thus, to observe the lowest 20 resonances for a sapphire, for example, the observable range would be from about 0.3 MHz to 1.5 MHz. The lowest observable mode for a diamond of this weight is about 1.2 MHz. The shape also dictates how low a mode can exist. A thinner shape will have a lower resonance than a round, for example.

FIG. 3B shows an example fingerprint spectrum including the in-phase and out-of-phase signals (using equation Sum=√((1 signal$^2$)+(2 signal$^2$)) for a 1.22 carat blue sapphire. The chart shows amplitude in volts 360 for the Y axis and frequency in Hz on the x axis 350. In the example fingerprint chart, multiple peaks, such as the highest peak 370 were detected. The example shows 180 distinct peaks.

Thus, FIG. 3B demonstrates how different stones, other than diamonds may also be subjected to the RUS systems and methods here to ascertain unique fingerprints of the stones for identification, analysis, valuation, etc.

Figure 4:
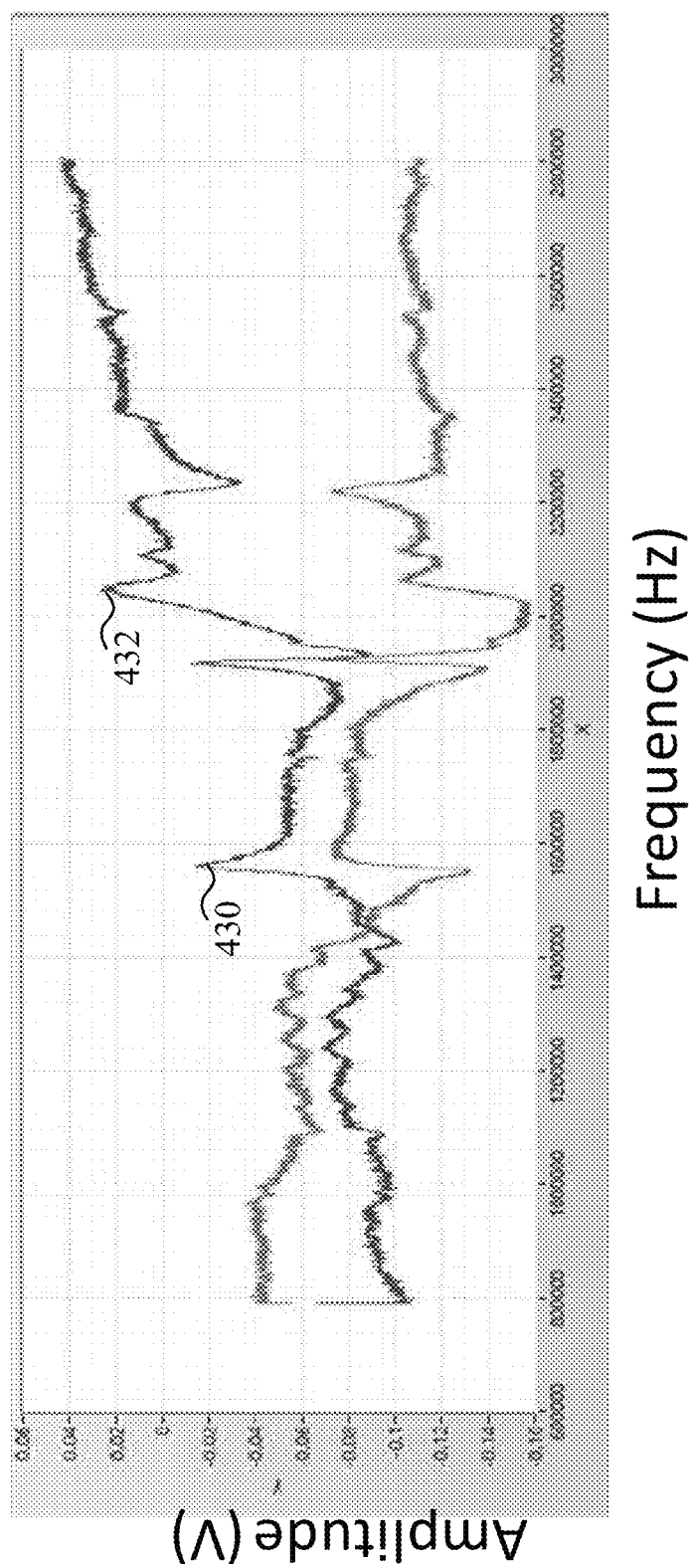
FIGS. 4-6 are example charts which may be ascertained using the systems and methods described herein.

FIG. 4 shows an example fingerprint of a rough coated diamond indicating cracks, but with some identifiable resonances. As can be seen, the peaks 430, 432 are rough, jagged and wider than those in FIG. 2. This is due to the physical makeup of the stone and its imperfections such as inclusions found in it. The wider peaks in FIG. 4 may affect the Q ratings as described herein.

Rough stones may exhibit resonances if the crystal(s) contained are sufficiently large and incipient cracks are few. If too many cracks are present in the stone, the resonance spectrum may lack enough details used to identify it. Such analysis may also ascertain any manipulation of the stone, or changes it has undergone since a set of earlier fingerprints were taken.

Figure 5A:
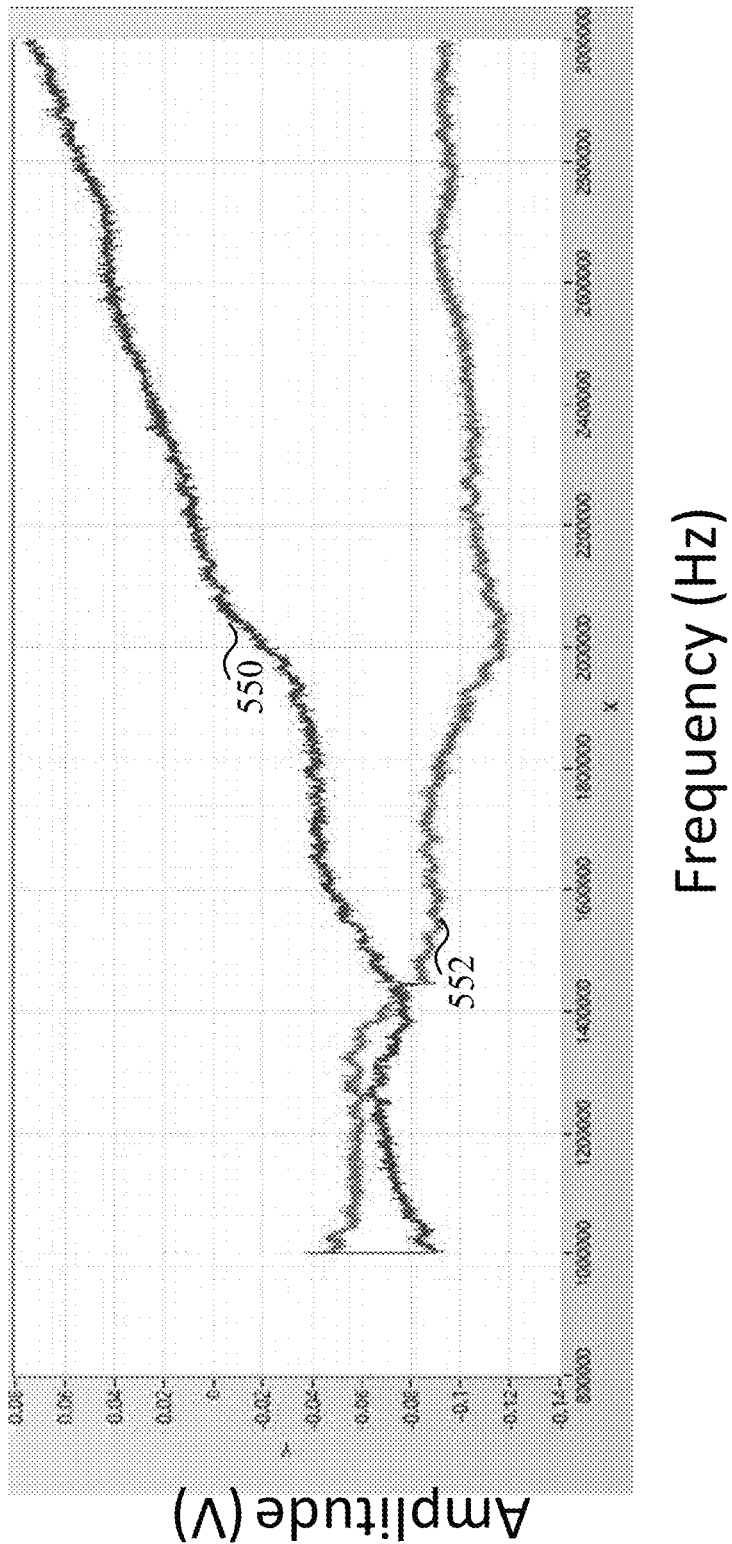

FIG. 5A shows an example fingerprint of a typical rough diamond with no discernable resonances. Both in phase 550 and quadrature 552 signals are graphed, but no discernible peaks are evident over the range. About 25% of the rough stones show no large crystal structures because significant resonances are not present due to numerous cracks. There should be no need to fingerprint these stones as they will likely be ground into diamond dust.

Figure 5B:
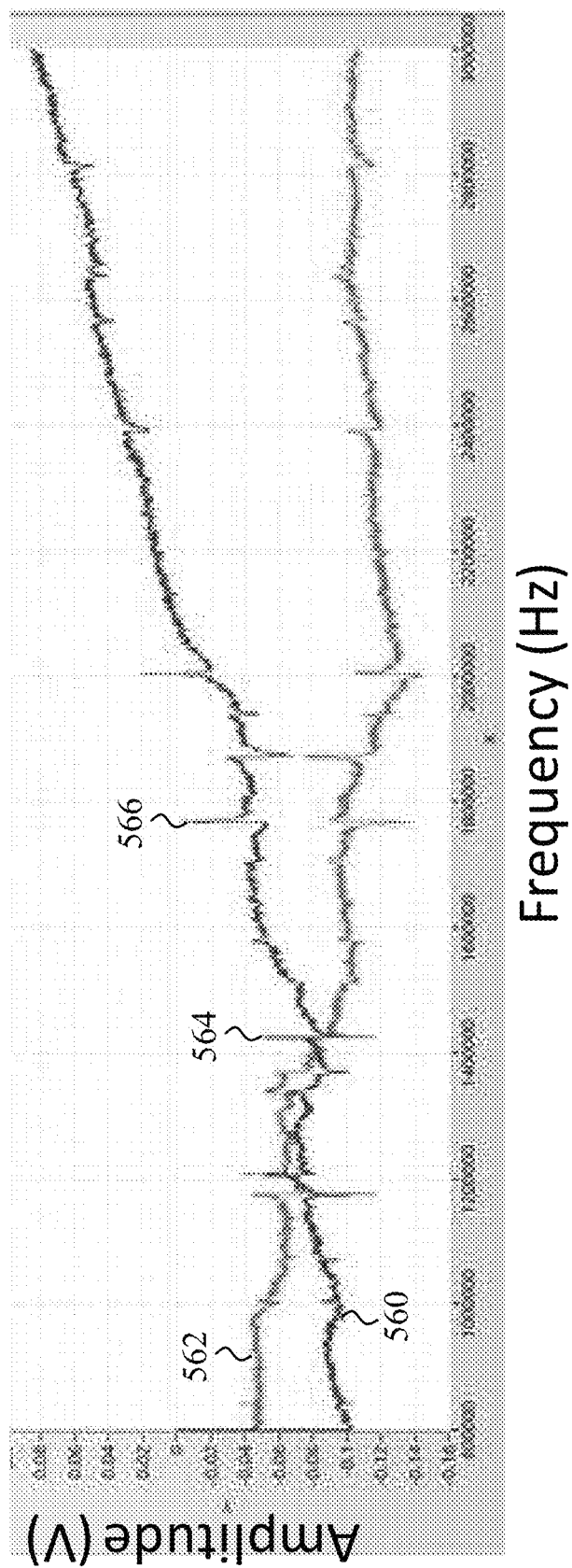

FIG. 5B shows an example fingerprint of an industrial quality coated stone both in phase 560 and quadrature 562. This graph shows a number of well-defined resonances 564, 566, but each peak is substantially broader than in a cut/polished stone that we know contains no cracks like FIG. 2. These stones can be fingerprinted and tracked.

Quality of Resonance Examples

In some examples, there may be variability in the detected peak position during RUS. In addition to and/or alternatively, the resultant resonance spectrum graph may be analyzed not only by identification of peak resonances, but the properties of the peak resonances themselves may be analyzed. By examining the standard deviation of peak positions as well as the peak width, another analysis may be performed. Such an analysis or "Q determination" may aid in consistency of measurement of resonant frequencies despite minor differences in diamond placement during testing and environmental conditions. This may indicate specific qualities or characteristics of the stone under evaluation.

In some examples, Q may be defined as the center frequency of a peak divided by the full width of the peak at half of its maximum.

$$Q = \text{peak frequency/full width at half maximum}$$

In other words, the peak width at half way up the peak may be analyzed to determine a Q. High Q resonances may be those that have high values, therefore are narrow, and low Q broad, from which the quality, and center frequency, may be accurately measured.

For example, when a resonance frequency graph shows a clear center, it can be said that the quality or Q of the fingerprint is higher than if the resonance center frequency is wider and harder to ascertain. Thus, wider resonance graph peaks have a lower Q rating which indicates a lower clarity grade in the stone.

Such a Q may be used in establishing a unique fingerprint, in that it may help define the accuracy of the measurement. For example, cut, polished diamonds exhibit Q's on the order of 10,000-50,000, whereas cut, polished diamonds of either small size or with low clarity and many inclusions have Q values on the order of 500-1000.

Referring back to FIG. 3 shows an example graph of resultant frequencies for a 0.50 carat diamond given a flawless grade. The graph shows that there are 10 peak resonances between 1.0 MHz and 3.0 MHz show Q's of $10^4$.

In addition, rough stones often contain cracks. When cut, an expert may detect these flaws and may be able to cut single crystals from a raw stone. The effect on the resonance spectrum is to substantially lower the Q by a factor of 10 or more (as shown by an example fingerprint graph in FIG. 4). Since many resonances exist in a narrow bandwidth (for example, 10 between 1 MHz and 3 MHz for a 0.5 carat sample), there may be several frequencies from which such frequency selections can be made as input energy described herein.

Fingerprint Comparison Examples

In some example embodiments, both an Absolute Frequency fingerprint and a Q fingerprint may be received and analyzed for identification purposes. For example, spectra graphs may be produced by the methods described above, and displayed for comparison. In example comparisons, the number of peak resonances which are the same for two different 1 carat stones is on the order of one in $10^6$. Therefore, statistically, this method may be used with a high degree of certainty that matches are accurate.

In some examples, the graphs themselves may be saved in libraries and cataloged to use as comparisons for stones. In some examples, instead of entire graphs stored in such libraries, additionally or alternatively, matrices may be built with specific resonance peaks indicated in amplitude and input frequency. In such matrices, only a few data points may need to be saved to compare later.

In some examples, such a comparison may be achieved by a computer algorithm. In such examples, a method to identify the absolute frequency may be used. In such examples, comparison of the peak resonances of a graph may be conducted. A comparison using a standard deviation may be used to match graphs. In some examples, the standard deviation tolerance is +/−200 Hz. In some examples, the tolerance may be different, based on the weight of the stone. For example, a larger stone (>1 carat) may produce more resonance peaks and require a smaller tolerance. A smaller stone (<1 carat) may produce fewer resonance peaks and require a larger standard deviation tolerance.

Figure 6:
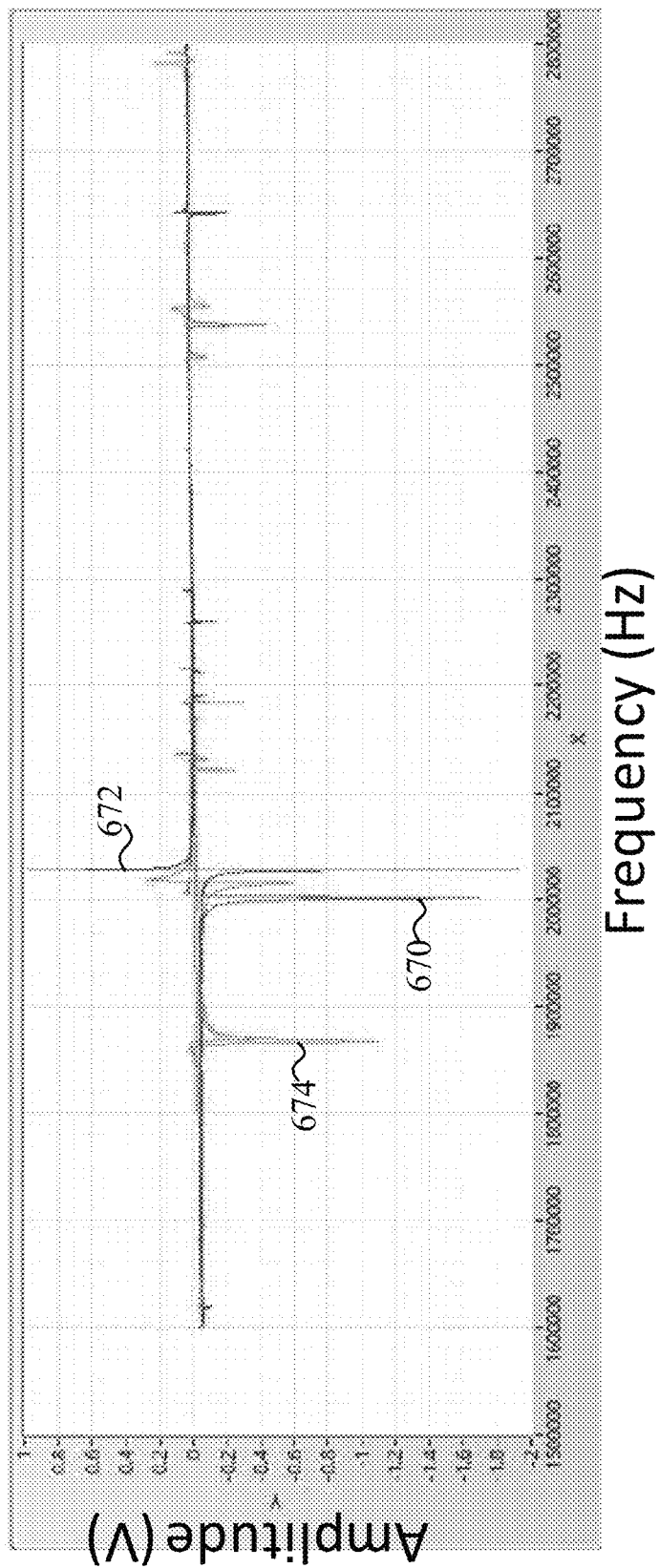

FIG. 6 shows an example fingerprint of three nearly identical 0.50 carat samples that produce different resonance graph patterns due to differences in the stones' geometries. Although flawless is a term of art, such gems are often not completely homogeneous due to the incorporation of foreign materials during the growth process or deviations from the perfect crystal lattice, in polished gems, these inclusions and inhomogeneities are low compared with rough gems. But in comparing RUS graphs, these gems can be differentiated. In FIG. 6, the red, 670 blue 672 and green 674 traces represent three different diamonds. Thus, even if the stones look similar to a human inspector, they can be differentiated by the RUS systems and methods.

Additionally, it may be useful to display multiple spectra on a single user interface graph, such as the example shown in FIG. 6. In FIG. 6, three nearly identical 0.50 ct cut, round diamonds are fingerprinted and displayed. A computer may be configured to accept or reject samples based on spectral differences.

Example Computing Device

Figure 7:
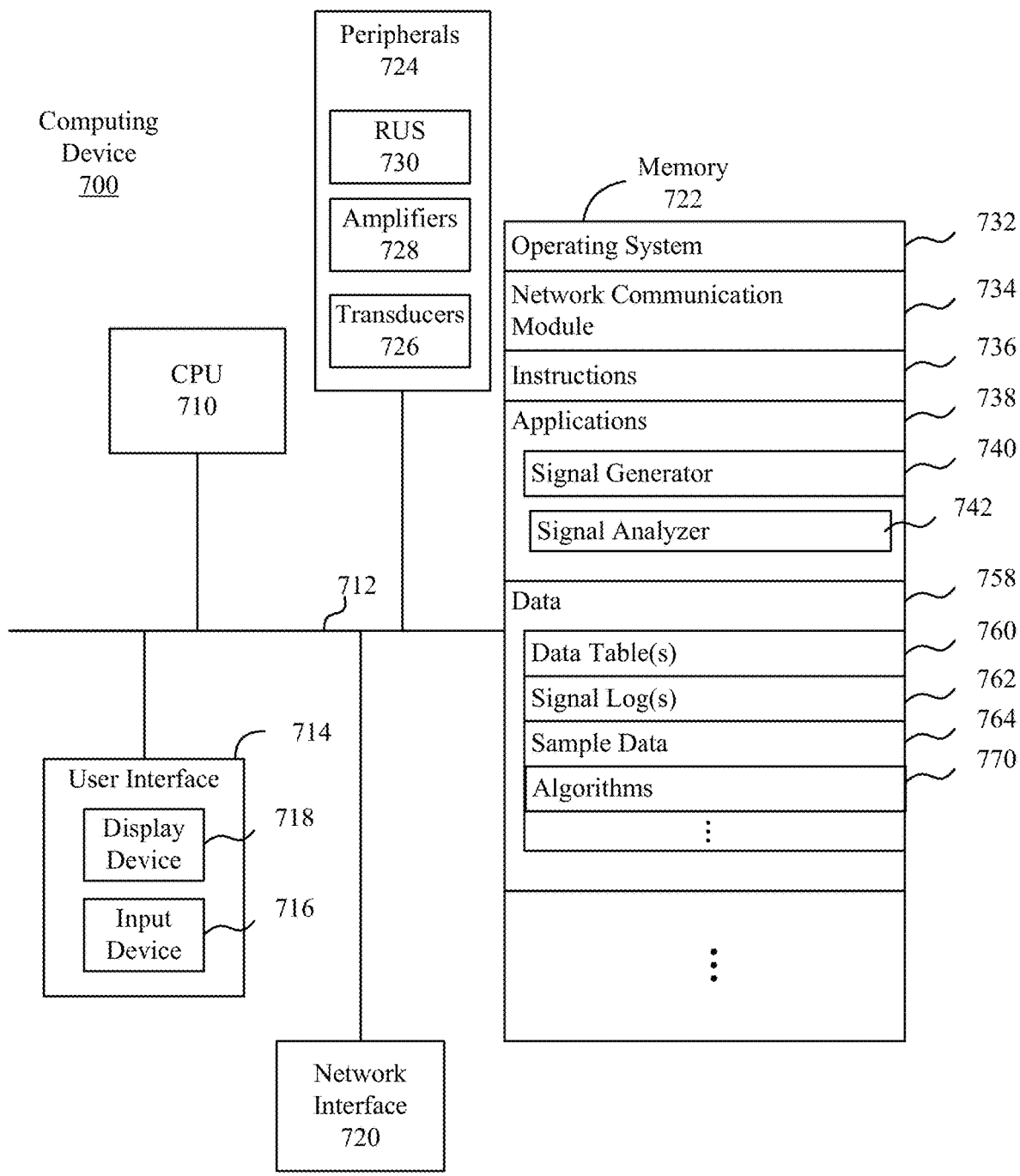
FIG. 7 is an example computer system which may be used to implement the methods described herein.

FIG. 7 shows an example computer 700 which may be used in practicing example embodiments described herein such as FIG. 1A and FIG. 1B. Such a computer 700 may be any kind of portable, desktop, distributed, or network based computing device. Such a system 700 may be configured to receive and analyze signal data as described herein, as well as generate resultant fingerprint graphs and display them in GUIs. Such a computer 700 may be a mobile device used to generate signals and receive signals as well as send and receive data, store data, analyze the data and cause display of GUIs representing data.

In FIG. 7, the computing device could be any kind such as but not limited to a smartphone, a laptop, tablet computer, server computer, or any other kind of computing device. The example shows a processor CPU 710 which could be any number of processors in communication via a bus 712 or other communication with a user interface 714. The user interface 714 could include any number of display devices 718 such as a screen which may be remotely located or locally located. The user interface 714 may also include an input such as a touchscreen, keyboard, mouse, pointer, buttons or other input devices.

FIG. 7 and the computer system 700 also includes a network interface 720 which may be used to interface with any wireless or wired network in order to transmit and receive data. Such an interface may allow for a smartphone, for example, to interface a cellular network and/or WiFi network and thereby the Internet. The example computing device 700 also shows peripherals 724 which could include any number of other additional features such as but not limited to an antenna for communicating wirelessly such as over cellular, WiFi, NFC, Bluetooth, infrared, or any combination of these or other wireless communications. In some examples, peripherals may include any number of RUS chips 730, amplifiers 728, transducers 726 for sending and receiving signals as described herein. In some example embodiments, as shown in FIG. 1A, the RUS chips 730 are in communication with the computer 700 and the RUS chip is in communication with the amplifiers 728 which in turn are in communication with the transducers 726 respectively. The example of peripherals 724 in FIG. 7 is not intended to be limiting, but only an example, alternatively or additionally, to the arrangements in FIG. 1A-1C.

The computing device 700 also includes a memory 722 which includes any number of operations executable by the processor 710. The memory in FIG. 7 shows an example operating system 732, network communication module 734, instructions for other tasks 738 and applications 738 such as signal generator 740 and/or signal analyzer 742. Also included in the example is for data storage 758. Such data storage may include data tables 760, signal logs 762, sample data 764 and/or stored algorithms 770 for use in the methods described herein.

CONCLUSION

The foregoing description, for purpose of explanation, has been described with reference to specific embodiments. However, the illustrative discussions above are not intended to be exhaustive or to limit the invention to the precise forms disclosed. Many modifications and variations are possible in view of the above teachings. The embodiments were chosen and described in order to best explain the principles of the invention and its practical applications, to thereby enable others skilled in the art to best utilize the invention and various embodiments with various modifications as are suited to the particular use contemplated.

The innovations herein may be implemented via one or more components, systems, servers, appliances, other sub-components, or distributed between such elements. When implemented as a system, such systems may include an/or involve, inter alia, components such as software modules, general-purpose CPU, RAM, etc. found in general-purpose computers. In implementations where the innovations reside on a server, such a server may include or involve components such as CPU, RAM, etc., such as those found in general-purpose computers.

Additionally, the innovations herein may be achieved via implementations with disparate or entirely different software, hardware and/or firmware components, beyond those set forth above. With regard to such other components (e.g., software, processing components, etc.) and/or computer-readable media associated with or embodying the present inventions, for example, aspects of the innovations herein may be implemented consistent with numerous general purpose or special purpose computing systems or configurations. Various exemplary computing systems, environments, and/or configurations that may be suitable for use with the innovations herein may include, but are not limited to: software or other components within or embodied on personal computers, servers or server computing devices such as routing/connectivity components, hand-held or laptop devices, multiprocessor systems, microprocessor-based systems, set top boxes, consumer electronic devices, network PCs, other existing computer platforms, distributed computing environments that include one or more of the above systems or devices, etc.

In some instances, aspects of the innovations herein may be achieved via or performed by logic and/or logic instructions including program modules, executed in association with such components or circuitry, for example. In general, program modules may include routines, programs, objects, components, data structures, etc. that perform particular tasks or implement particular instructions herein. The inventions may also be practiced in the context of distributed software, computer, or circuit settings where circuitry is connected via communication buses, circuitry or links. In distributed settings, control/instructions may occur from both local and remote computer storage media including memory storage devices.

Innovative software, circuitry and components herein may also include and/or utilize one or more type of computer readable media/medium. Computer readable media can be any available media that is resident on, associable with, or can be accessed by such circuits and/or computing components. By way of example, and not limitation, computer readable media may comprise computer storage media and communication media. Computer storage media includes volatile and nonvolatile, removable and non-removable media implemented in any method or technology for storage of information such as computer readable instructions, data structures, program modules or other data. Computer storage media includes, but is not limited to, RAM, ROM, EEPROM, flash memory or other memory technology, CD-ROM, digital versatile disks (DVD) or other optical storage, magnetic tape, magnetic disk storage or other magnetic storage devices, or any other medium which can be used to store the desired information and can accessed by computing component. Communication media may comprise computer readable instructions, data structures, program modules and/or other components. Further, communication media may include wired media such as a wired network or direct-wired connection, however no media of any such type herein includes transitory media. Combinations of the any of the above are also included within the scope of computer readable media.

In the present description, the terms component, module, device, etc. may refer to any type of logical or functional software elements, circuits, blocks and/or processes that may be implemented in a variety of ways. For example, the functions of various circuits and/or blocks can be combined with one another into any other number of modules. Each module may even be implemented as a software program stored on a tangible memory (e.g., random access memory, read only memory, CD-ROM memory, hard disk drive, etc.) to be read by a central processing unit to implement the functions of the innovations herein. Or, the modules can comprise programming instructions transmitted to a general purpose computer or to processing/graphics hardware via a transmission carrier wave. Also, the modules can be implemented as hardware logic circuitry implementing the functions encompassed by the innovations herein. Finally, the modules can be implemented using special purpose instructions (SIMD instructions), field programmable logic arrays or any mix thereof which provides the desired level performance and cost.

As disclosed herein, features consistent with the present inventions may be implemented via computer hardware, software and/or firmware. For example, the network systems and methods disclosed herein may be embodied in various forms including, for example, a data processor, such as a computer that also includes a database, digital electronic circuitry, firmware, software, or in combinations of them. Further, while some of the disclosed implementations describe specific hardware components, systems and methods consistent with the innovations herein may be implemented with any combination of hardware, software and/or firmware. Moreover, the above-noted features and other aspects and principles of the innovations herein may be implemented in various environments. Such environments and related applications may be specially constructed for performing the various routines, processes and/or operations according to the invention or they may include a general-purpose computer or computing platform selectively activated or reconfigured by code to provide the necessary functionality. The processes disclosed herein are not inherently related to any particular computer, network, architecture, environment, or other apparatus, and may be implemented by a suitable combination of hardware, software, and/or firmware. For example, various general-purpose machines may be used with programs written in accordance with teachings of the invention, or it may be more convenient to construct a specialized apparatus or system to perform the required methods and techniques.

Aspects of the method and system described herein, such as the logic, may also be implemented as functionality programmed into any of a variety of circuitry, including programmable logic devices ("PLDs"), such as field programmable gate arrays ("FPGAs"), programmable array logic ("PAL") devices, electrically programmable logic and memory devices and standard cell-based devices, as well as application specific integrated circuits. Some other possibilities for implementing aspects include: memory devices, microcontrollers with memory (such as EEPROM), embedded microprocessors, firmware, software, etc. Furthermore, aspects may be embodied in microprocessors having software-based circuit emulation, discrete logic (sequential and combinatorial), custom devices, fuzzy (neural) logic, quantum devices, and hybrids of any of the above device types. The underlying device technologies may be provided in a variety of component types, e.g., metal-oxide semiconductor field-effect transistor ("MOSFET") technologies like complementary metal-oxide semiconductor ("CMOS"), bipolar technologies like emitter-coupled logic ("ECL"), polymer technologies (e.g., silicon-conjugated polymer and metal-conjugated polymer-metal structures), mixed analog and digital, and so on.

It should also be noted that the various logic and/or functions disclosed herein may be enabled using any number of combinations of hardware, firmware, and/or as data and/or instructions embodied in various machine-readable or computer-readable media, in terms of their behavioral, register transfer, logic component, and/or other characteristics. Computer-readable media in which such formatted data and/or instructions may be embodied include, but are not limited to, non-volatile storage media in various forms (e.g., optical, magnetic or semiconductor storage media) though again does not include transitory media/medium. Unless the context clearly requires otherwise, throughout the description, the words "comprise," "comprising," and the like are to be construed in an inclusive sense as opposed to an exclusive or exhaustive sense; that is to say, in a sense of "including, but not limited to." Words using the singular or plural number also include the plural or singular number respectively. Additionally, the words "herein," "hereunder," "above," "below," and words of similar import refer to this application as a whole and not to any particular portions of this application. When the word "or" is used in reference to a list of two or more items, that word covers all of the following interpretations of the word: any of the items in the list, all of the items in the list and any combination of the items in the list.

Although certain presently preferred implementations of the invention have been specifically described herein, it will be apparent to those skilled in the art to which the invention pertains that variations and modifications of the various implementations shown and described herein may be made without departing from the spirit and scope of the invention. Accordingly, it is intended that the invention be limited only to the extent required by the applicable rules of law.

What is claimed is:

1. A method, comprising:
   by a signal generator and a signal processor,
      sending an input signal to a first input transducer,
   wherein the first input transducer is contacting a gemstone under evaluation;
   receiving a resonance signal from a second receiver transducer,
      wherein the second receiver transducer is contacting the gemstone under evaluation;
   stepping the input signal through a range of sinusoidal input frequencies at a 100 Hz interval, from a range either 1 MHz to 4 MHz if the gemstone is less than one carat size, or from a range 0.2 MHz to 0.3 MHz if the gemstone is greater than one carat in size;
   receiving a range of received signals;
   processing, with algorithms, the range of received signals by using a square root of a sum of squares of the received signals for producing graphs of all positive values;
   determining, by the computer, resonant frequencies of the gemstone by identifying spikes of highest peaks in the display of all positive values;
   determining how many crystals are included in the gemstone by counting the identified spikes of highest peaks in the display of all positive values;
   determining a Q rating using the received signals wherein Q is defined as the center frequency of a peak divided by the full width at half maximum of the peak;
   establishing a unique fingerprint for the gemstone based on the range of received signals and the Q value;
   determining a weight approximation of the gemstone using a square root of a mass divided by two for a lowest resonance frequency spike detected; and
   sending the processed range of received signals for the gemstone under evaluation to a computer storage for storage and display of all positive values.

2. The method of claim 1 wherein the input signal is sent from the signal generator to the first transducer through an input amplifier; and
   wherein the received signal is received at the signal processor from the receiver transducer through a receiver amplifier.

3. The method of claim 1 wherein processing the received signal includes in-phase and quadrature components of the received signal.

4. The method of claim 1 wherein the signal processor includes a phase sensitive detector and digital signal processor.

5. The method of claim 1 wherein stepping the input signal through a range of input frequencies is stepped by 1 to 1000 Hz.

6. The method of claim 1 wherein the range of input frequencies is between 0.1 MHz and 4 MHz.

7. The method of claim 1 wherein the signal generator and the signal processor are configured on a chip, with a processor and memory.

8. A non-transitory computer-readable medium having computer-executable instructions thereon for a method, the method comprising:
   by a signal generator and a signal processor,
      sending an input signal to a first input transducer,
   wherein the first input transducer is contacting a gemstone under evaluation;
   receiving a resonance signal from a second receiver transducer,
      wherein the second receiver transducer is contacting the gemstone under evaluation;
   stepping the input signal through a range of input frequencies at a 200 Hz interval, from a range either greater than 1 MHz if the gemstone is less than one carat size, or from a range less than 1 MHz if the gemstone is greater than one carat in size;
   receiving a range of received signals;
   processing, with algorithms, the range of received signals;
   determining, by the computer, resonant frequencies of the gemstone by identifying spikes of highest peaks in the display of all positive values;
   determining how many crystals are included in the gemstone by counting the identified spikes of highest peaks in the display of all positive values;
   determining a Q rating using the received signals wherein Q is defined as the center frequency of a peak divided by the full width at half maximum of the peak;

establishing a unique fingerprint for the gemstone based on the range of received signals and the Q value;

determining a weight approximation of the gemstone using a square root of a mass divided by two for a lowest resonance frequency spike detected; and sending the processed range of received signals for the gemstone under evaluation to a computer for display and storage.

9. The non-transitory computer-readable medium of claim 8 wherein the input signal is sent from the signal generator to the first transducer through an input amplifier; and wherein the received signal is received at the signal processor from the receiver transducer through a receiver amplifier.

10. The non-transitory computer-readable medium of claim 8 wherein processing the received signal includes in-phase and quadrature components of the received signal.

11. The non-transitory computer-readable medium of claim 8 wherein the signal processor includes a phase sensitive detector and digital signal processor.

12. The non-transitory computer-readable medium of claim 8 wherein stepping the input signal through a range of input frequencies is stepped by 1 to 1000 Hz.

13. The non-transitory computer-readable medium of claim 8 wherein the range of input frequencies is between 0.1 and 4 MHz.

14. The non-transitory computer-readable medium of claim 13 wherein stepping the input signal through a range of input frequencies is stepped by 1 to 1000 Hz.

15. The non-transitory computer-readable medium of claim 8 wherein the signal generator and the signal processor are configured on a chip, with a processor and memory.

16. A system, comprising:

a chip, with a processor and memory, the chip configured as a signal generator and a signal processor, to send an input signal to a first input transducer, which may be amplified, wherein the first input transducer is in contact with a gemstone under evaluation;

receive a resonance signal from a second receiver transducer, wherein the second receiver transducer, which may be amplified, is in contact with the gemstone under evaluation;

step the input signal through a range of input frequencies at an interval between 100 Hz and 300 Hz, from a range based on a size of the gemstone;

receive a range of received signals;

process, with algorithms, the range of received signals;

determine, by the computer, resonant frequencies of the gemstone by identifying spikes of highest peaks in the display of all positive values;

determine how many crystals are included in the gemstone by counting the identified spikes of highest peaks in the display of all positive values;

determine a Q rating using the received signals, wherein Q is defined as the center frequency of a peak divided by the full width at half maximum of the peak;

establish a unique fingerprint for the gemstone based on the range of received signals and the Q value;

determine a weight approximation of the gemstone using a square root of a mass divided by two for a lowest resonance frequency spike detected; and send the processed range of received signals for the gemstone under evaluation to a computer for display and storage.

17. The system of claim 16 wherein the input signal step through a range of input frequencies is stepped by 100 Hz.

18. The system of claim 16 wherein the process of the received signal includes in-phase and quadrature components of the received signal.

19. The system of claim 16 wherein the signal processor includes a phase sensitive detector and digital signal processor.

20. The method of claim 1 wherein the Q rating is peak frequency divided by full width at half maximum.

\* \* \* \* \*